(12) United States Patent
Iles et al.

(10) Patent No.: US 10,359,431 B2
(45) Date of Patent: Jul. 23, 2019

(54) METHOD FOR DETECTING ABNORMALITIES IN HEMOGLOBIN

(71) Applicant: Map IP Holding Limited, Cambridgeshire (GB)

(72) Inventors: Raymond Kruse Iles, Cambridgeshire (GB); Jason Kruse Iles, Cambridgeshire (GB); Thomas Abban, Cambridgeshire (GB); Suzanne Margaret Elizabeth Docherty, Cambridgeshire (GB); Mahmoud Naase, Cambridgeshire (GB)

(73) Assignee: Map IP Holding Limited, Ely (GB)

( * ) Notice: Subject to any disclaimer, the term of this patent is extended or adjusted under 35 U.S.C. 154(b) by 72 days.

(21) Appl. No.: 15/506,730

(22) PCT Filed: Aug. 27, 2015

(86) PCT No.: PCT/GB2015/052491
§ 371 (c)(1),
(2) Date: Feb. 25, 2017

(87) PCT Pub. No.: WO2016/030688
PCT Pub. Date: Mar. 3, 2016

(65) Prior Publication Data
US 2018/0224462 A1 Aug. 9, 2018

(30) Foreign Application Priority Data
Aug. 29, 2014 (GB) .................................. 1415367.0

(51) Int. Cl.
*G01N 33/68* (2006.01)
*G01N 33/72* (2006.01)

(52) U.S. Cl.
CPC ....... *G01N 33/6851* (2013.01); *G01N 33/721* (2013.01)

(58) Field of Classification Search
None
See application file for complete search history.

(56) References Cited

U.S. PATENT DOCUMENTS 3,492,095 A * 1/1970 Tillen .................. G01N 33/721
436/164
4,847,209 A 7/1989 Lewis
(Continued)

FOREIGN PATENT DOCUMENTS

WO 2012166055 12/2012

OTHER PUBLICATIONS

Griffin, N.M. et al. Label-free, normalized quantification of complex mass spectrometry data for proteomic analysis, Nature Biotechnology, vol. 28(1), pp. 83-91 (Year: 2010).*

(Continued)

*Primary Examiner* — Xiaoyun R Xu
(74) *Attorney, Agent, or Firm* — Diederiks & Whitelaw, PLC.

(57) ABSTRACT

The method describes rapid screening of whole blood samples, pin prick and blood spot cards, subjected to MALDI-ToF Mass spectrometry. The spectra is generated and compared to those from normal healthy controls. Characteristic spectra are indicative of the presence of a hemoglobinopathy and the method can be used to screen/diagnose all sickle cell diseases, alpha and beta Thalassemias.

10 Claims, 11 Drawing Sheets

(56) References Cited

U.S. PATENT DOCUMENTS

| | | |
|---|---|---|
| 2004/0171026 A1 | 9/2004 | Hochstrasser |
| 2006/0020440 A1 | 1/2006 | Hellerstein |
| 2009/0093066 A1 | 4/2009 | Blackshear |
| 2010/0184658 A1 | 7/2010 | Gelber |
| 2010/0330594 A1 | 12/2010 | Hart |
| 2011/0053191 A1 | 3/2011 | Hess |
| 2011/0250618 A1 | 10/2011 | Nelson |
| 2012/0107859 A1 | 5/2012 | Petrotchenko |

OTHER PUBLICATIONS

Williams, P.J., et al. Advances in Native Mass Spectrometry Based Methods for the Analysis of Non-Covalent Protein Complexes, Waters. retrieved from internet http://waters.info/webassets/cms/library/docs/2014asms_williams_advances_in_native.pdf (Year: 2014).*

P. Kleinert et al., "Mass Spectrometry: A Tool for Enhanced Detection of Hemoglobin Variants", Clinical Chemistry, 2007, 54(1):69-76.

J. Hachani et al., "Maldi-TOF MS profiling as the first-tier screen for sickle cell disease in neonates: matching throughput to objectives", Proteomics—Clinical Applications, 2011, 5:7-8.

I. Zanella-ZCleon et al., "Phenotype determination of hemoglobinopathies by mass spectrometry", Clinical Biochemistry, 2009, 42(18):1807-1817.

H. Troxler et al., "Advances in hemoglobinopathy detection and identification", Advances in Clinical Chemistry, 2002, 57:1-28.

Office Action dated Jul. 12, 2018 in U.S. Appl. No. 15/506,731.

Faynor, "Clinical Pathology Rounds: Glycosylated Hemoglobin Electrophoresis", Laboratory Medicine, 1997, 28(6), pp. 370-373.

Hattan et al., "Analysis and Quantitation of Glycated Hemoglobin by Matrix Assisted Laser Desorption/Ionization Time of Flight Mass Spectrometry", American Society for Mass Spectrometry, 2016, 27, pp. 532-541.

Notice of Allowance dated Oct. 17, 2018 in related U.S. Appl. No. 15/506,731.

Algahtani, et al., "Use of Glycated Hemoglobin in the Diagnosis of Diabetes Mellitus and Pre-diabetes and Role of Fasting Plasma Glucose, Oral Glucose Tolerance Test", 2013, International Journal of Preventative Medicine, 4(9), pp. 1025-1029.

Bahar, A. et al., "Relationship Between Beta-Globin Gene Carrier State and Insulin Resistance", 2012, Journal of Diabetes and Metabolic Disorders, 11(22), http://www.jdmdonline.com/content/11/1/22.

Office Action dated Oct. 25, 2017 in related U.S. Appl. No. 15/506,731.

Biroccio A., et al., "A quantitative method for the analysis of glycated and glutathionylated hemoglobin by matrix-assisted laser desorption ionization-time of flight mass spectrometry", 2005, Analytical Biochemistry, 336(2), pp. 279-288.

D'Alessandro, A., et al., "Haemoglobin glycation (Hb1Ac) increases during red blood cell storage: a MALDI-TOF mass-spectrometry-based investigation", 2013, Vox Sanguinis, 105(2), pp. 177-180.

Lapolla A., et al., "A matrix-assisted laser desorption/ionization mass spectrometry study of the non-enzymatic glycation products of human globins in diabetes", 2005, Rapid Communications in Mass Spectrometry, 19(2), pp. 162-168.

Lapolla A., et al., "Protein glycation in diabetes as determined by mass spectrometry", 2013, International Journal of Endocrinology, 49(9), pp. 1399-1311.

* cited by examiner

Figure 1 Diagrammatic representation of the major functional β and α genes of human haemoglobin.

Figure 2 Spectra of normal HbA whole blood

Figure 3 Spectra of HbAS

Figure 4 Spectra of HbSC

Figure 5 Spectra of HbAC

Figure 6 Spectra of HbAE

Figure 7 Spectra of HbF

Figure 8 Spectra of HbAH

Figure 9 Spectra of HbAG

Figure 10 Spectra of HbA/Kenya phenotype

FIG. 11A

A) - Phenotypic normal blood samples

| Assigned Peak | m/z | Cntrl-1 | Cntrl-2 | Cntrl-3 | Cntrl-4 | Cntrl-5 | Cntrl-6 | Cntrl-7 | Cntrl-8 | Cntrl-9 | Average | SD |
|---|---|---|---|---|---|---|---|---|---|---|---|---|
| Relative to α-globin | | | | | | | | | | | | |
| α-globin | 7564 | 100 | 100 | 100 | 100 | 100 | 100 | 100 | 100 | 100 | | |
| Acetyl/Carb α-globin | 7594 | 0 | 0 | 0 | 1.8 | 1.9 | 5.8 | 5 | 3.9 | 4 | 2.49 | 2.26 |
| αGlc -globin | 7645 | 1.78 | 1.6 | 1.4 | 3 | 2 | 1 | 2.8 | 1.96 | 0.5 | 1.78 | 0.79 |
| α-globin SA adduct | 7671 | 10.9 | 11.2 | 12.6 | 11.6 | 10.6 | 10.7 | 10 | 11.7 | 15 | 11.59 | 1.48 |
| β-globin | 7936 | 70.9 | 53.8 | 85.9 | 91.3 | 69.9 | 90.2 | 84 | 81.2 | 76.4 | 78.18 | 11.93 |
| Relative to β/Sβ-globin | | | | | | | | | | | | |
| Sβ-globin | 7921 | 0 | 0 | 0 | 0 | 0 | 0 | 0 | 0 | 0 | | |
| β-globin | 7936 | 100 | 100 | 100 | 100 | 100 | 100 | 100 | 100 | 100 | | |
| δ-globin | 7965 | 3 | 0 | 0 | 5.2 | 2.7 | 6.2 | 9.2 | 5 | 6 | 4.14 | 3.02 |
| Gγ-globin | 7999 | 0 | 0 | 0 | 0 | 0 | 1 | 1 | 0 | 0 | 0.22 | 0.44 |
| Aγ-globin | 8005 | 0 | 0 | 0 | 0 | 0 | 0 | 0 | 0 | 0 | 0.00 | 0.00 |
| βGlc-globin | 8017 | 2.56 | 3.4 | 2 | 4.4 | 2.7 | 2.1 | 3.4 | 5.2 | 2.56 | 3.15 | 1.07 |
| β-globin SA adduct | 8039 | 10.25 | 12 | 16.3 | 14 | 11.2 | 11.1 | 13 | 15 | 18.6 | 13.49 | 2.75 |
| ? ε-globin | 8088 | 2.56 | 3.4 | 0 | 0 | 1.8 | 0 | 0 | 0 | 0 | 0.58 | 1.21 |

FIG. 11B

B) - Phenotypic abnormal blood samples

| Assigned Peak | m/z | SCD HbS | SCD HbSC | Beta-thalassemia trait | Beta-thalassemia | HbE disease | Alpha-thalassemia trait | Alpha-thalassemia trait | Average | SD |
|---|---|---|---|---|---|---|---|---|---|---|
| Relative to α-globin | | | | | | | | | | |
| α-globin | 7564 | 100 | 100 | 100 | 100 | 100 | 100 | 100 | | |
| Acetyl/Carb α-globin | 7594 | 2.12 | 1.8 | 2.7 | 0 | 5 | 5.9 | 5 | 3.2 | 2.14 |
| αGlc -globin | 7645 | 1 | 1.8 | 2.2 | 1.98 | 2.5 | 2.4 | 2.7 | 12.1 | 0.57 |
| α-globin SA adduct | 7671 | 11 | 12 | 11.9 | 12.2 | 10.6 | 12.8 | 12.1 | 11.8 | 0.75 |
| β-globin | | 60 | 43.9 | 66.6 | 63.1 | 47.75 | 66.3 | 59 | 58.1 | 8.92 |
| Relative to β/sβ-globin | | | | | | | | | | |
| sβ-globin | 7921 | 100 | 13.4 | 0 | 0 | 0 | 0 | 0 | | |
| β-globin | 7936 | 0 | 100 | 100 | 100 | 100 | 100 | 100 | | |
| δ-globin | 7965 | 7.1 | 6.3 | 6.18 | 5.6 | 13.3 | 9 | 8.3 | 8.0 | 2.64 |
| Gγ-globin | 7999 | 0 | 7.7 | 0 | 0 | 0 | 0 | 4.5 | 1.7 | 3.12 |
| Aγ-globin | 8005 | 21.4 | 0 | 0 | 0 | 0 | 0 | 0 | 3.1 | 8.09 |
| βGlc-globin | 8005 | 0 | 9.1 | 6 | 4.7 | 5.88 | 3.96 | 6.25 | 5.1 | 2.78 |
| β-globin SA adduct | 8039 | 14.2 | 14.7 | 12.9 | 12.5 | 13.3 | 10.9 | 16.7 | 13.6 | 1.84 |
| ? ε-globin | 8088 | 7.14 | 7 | 5.6 | 16.3 | 5.8 | 7.5 | 11.6 | 8.7 | 3.89 |

Figure 12 Formalin fixed blood

Figure 13 Spectra of formalin fixed and lysed whole blood Sickle Cell Disease

Figure 14 - Summary table of spectral peak analysis 30,000 to 100,000 m/z of formalin fixed blood (❖) and relative percentage abundance –

A) Phenotypic normal blood samples

| Assigned Peak | m/z | Cntrl-1 | Cntrl-2 | Cntrl-3 | Cntrl-4 | Cntrl-5 | Cntrl-6 | Cntrl-7 | Cntrl-9 | Average | SD |
|---|---|---|---|---|---|---|---|---|---|---|---|
| Relative to ❖dimer | | | | | | | | | | | |
| ❖Dimer | 32480 | 100 | 100 | 100 | 100 | 100 | 100 | 100 | 100 | | |
| ❖Trimer | 49000 | 9.6 | 5.6 | 1 | 1 | 6.5 | 5 | 7 | 5.6 | 5.42 | 2.85 |
| ❖s-tetramer | 64670 | 0.3 | 2.8 | 1.2 | 8.2 | 4.3 | 2 | 6 | 2.8 | 4.82 | 3.56 |
| ❖L-Tetramer | 69550 | 0.5 | 7 | 6 | 4 | 1.3 | 1 | 0 | 1.3 | 2.47 | 2.55 |

B) - Phenotypic abnormal blood samples

| Assigned Peak | m/z | SCD HbS | SCD HbSC | Beta-thalassemia trait | Beta-thalassemia | HbF disease | Alpha-thalassemia trait | Alpha-thalassemia trait | Average | SD |
|---|---|---|---|---|---|---|---|---|---|---|
| Relative to ❖dimer | | | | | | | | | | |
| ❖Dimer | 32480 | 100 | 100 | 100 | 100 | 100 | 100 | 100 | | |
| ❖Trimer | 49000 | 1 | 1 | 1 | 1 | 1 | 1 | 1 | 1.0 | 2.85 |
| ❖s-tetramer | 64670 | 13.3 | 16.8 | 20 | 23.3 | 10 | 19.5 | 15 | 16.7 | 3.56 |
| ❖L-Tetramer | 69550 | 155.5 | 44.73 | 40 | 4.1 | 14.4 | 4.1 | 17.8 | 40.1 | 2.55 |

METHOD FOR DETECTING ABNORMALITIES IN HEMOGLOBIN

CROSS-REFERENCE TO RELATED APPLICATIONS

This application is a 35 U.S.C. § 371 national phase application of PCT Application No. PCT/GB15/052491, filed Aug. 27, 2015, which claims priority to Great Britain Application No. 1415367.0, filed Aug. 29, 2014, each of which is incorporated herein by reference in its entirety.

The method describes rapid screening of whole blood samples, pin prick and blood spot cards, subjected to MALDI-ToF Mass spectrometry following:

1) lysis in distilled deionised water (or freezing) and massive dilution at the range of 1/10 to 1/8000 in either distilled deionised $H_2O$ or 0.1% TFA in distilled deionised $H_2O$. The resulting spectra is examined as singly charged ions at the Mass/charge range of 15000 m/z to 16,200 m/z; but preferably the doubly charged ions at 7550 to 8200 m/z.

2) Incubation with citrate buffered formalin followed by lysis in distilled deionised water (or freezing) and massive dilution at the range of 1/10 to 1/8000 in either distilled deionised $H_2O$ or 0.1% TFA in distilled deionised $H_2O$. The resulting spectra is examined as singly charged ions at the Mass/charge range of 15000 m/z to 100,000 m/z.

The spectra is generated using preferably sinapinic acid as matrix and characteristic spectra are indicative of the presence of an hemoglobinopathy and can screen/diagnose all sickle cell diseases, alpha and beta Thalassemias.

BACKGROUND

Hemoglobinopathies are the largest group of inherited human monogenic disorders worldwide and are due to mutations in one or more of the genes coding for the globin proteins that form the $\alpha 2\beta 2$ hetero-tetrameric complex that binds oxygen in red blood cells—hemoglobin. The resulting structural alteration in the patients (Hb) can be clinically mild, even occult, to being the cause of severe chronic morbidity and even neonatal death.

Within the Arabic nations hemoglobinopathies are the most common genetic diseases; with reported carrier rates of 1-11% for β-thalassaemia, 1-58% for α-thalassaemia and 0.3-30% for sickle cell trait.

In India the most common hemoglobinopathies are sickle cell trait, Hb D and Hb E. It was estimated that, in the year 2000, with a population of 1000 million and a birth rate of 25 per thousand, there would be about 45 million carriers and about 15,000 infants born in India each year with hemoglobinopathies.

Figure 1:
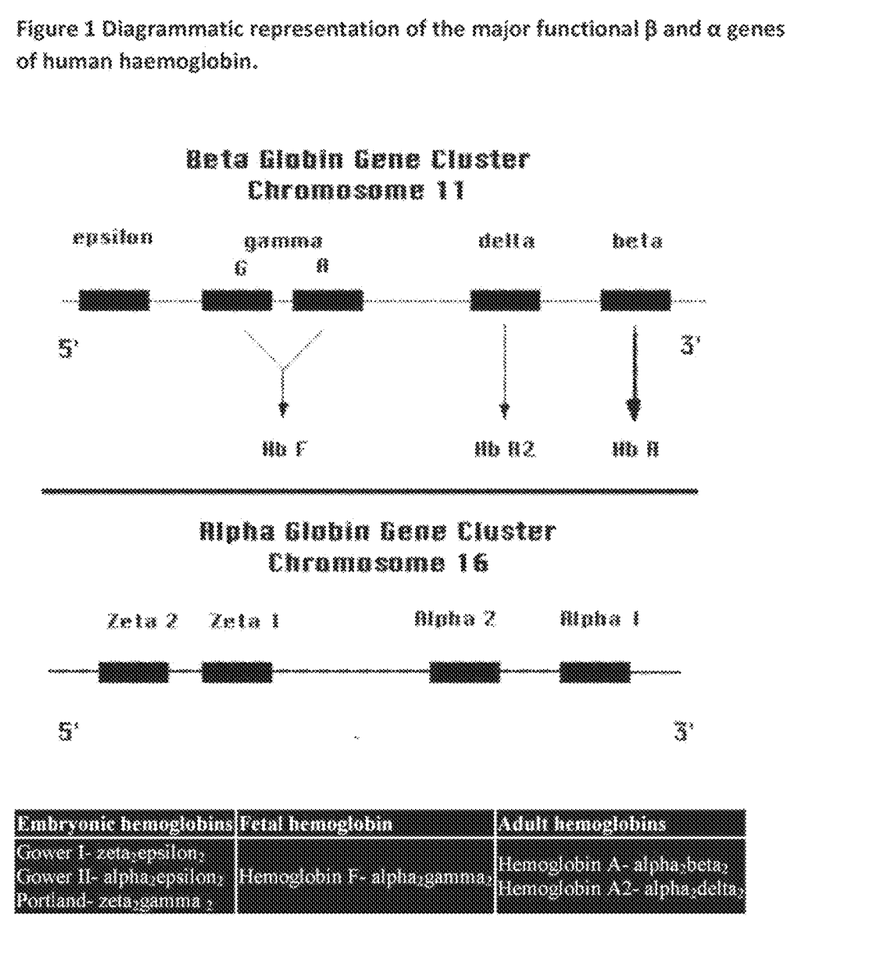
FIG. 1 shows a Simplified Diagrammatic representation of the functionally expressed Beta and Alpha-globin genes found in humans (omitted are the known pseudogenes within the gene clusters).

Hemoglobin itself should be a heterotetrameric complex containing two of alpha gene globin protein products associated with two beta gene globin proteins. The genetics and protein biochemistry of the constituent globin proteins are complex: human β-globin locus is composed of five genes located on a short region of chromosome 11, responsible for the creation of the beta parts of Hemoglobin. This locus contains not only the gene for the classic expressed beta (β) globin gene but also delta (δ), gamma-A (Aγ), gamma-G (Gγ), and epsilon globin (ε). The human α-globin gene cluster is found on chromosome 16 and contain expressed globin genes Alpha 1 (α1) and Alpha 2 (α2) and Zeta (ξ) (see FIG. 1) but a new α-globin gene has recently been identified termed Hb Mu (μ). As human life moves from early fetal to late pregnancy, birth and infant/adult life the alpha and beta gene pairing change to match the circumstance of in utero and extra utero life.

For example the very early embryo produces Hb combinations $\xi_2\varepsilon_2$ (Gower); $\alpha_2\varepsilon_2$ (Gower II) and $\xi_2\gamma_2$ (Portland) by the red blood stem cells formed in the Yolk sac during the first trimester of pregnancy. This is rapidly superseded by α2γ2 (HbF), produced by the red blood stem cells of the fetal liver during the second and third trimester. After birth this changes to predominantly $\alpha_2\beta_2$ (HbA), some $\alpha_2\delta_2$ (HbA2) and trace amounts of HbF (see FIG. 1).

Not surprisingly the various hemoglobinopathies identified were named as characteristics of the hetero-tetrameric hemoglobin complex rather than the feature of an isolated globin proteins. In Sickle cell disease the hemoglobin Hb S is where globin gene β has a specific amino acid change mutation β6Glu-Val at position 6 of the β globin protein and is termed Sβ; and the hetero-tetrameric Hb is $\alpha_2$ S$\beta_2$. Sickle cell trait being a complex of normal β and Sβ within the red cells constituent hemoglobin molecules as a result of heterozygosity and is often unnoticed. Hemoglobin C (HbC) is a structural variant of normal hemoglobin (HbA) caused by an amino acid substitution at position 6 of the β-globin chain (β6Glu-Lys). It is one of the most prevalent abnormal hemoglobin mutations globally alongside hemoglobin S, which occurs at the same position (HbS; β6Glu-Val), and hemoglobin E (HbE, β26Glu-Lys). In HbC heterozygote individuals (AC), this trait is asymptomatic. Homozygosity (CC) causes clinically mild haemolytic anaemia, due to the reduced solubility of the red blood cells which can lead to crystal formation. HbC is mainly of clinical significance when inherited in combination with HbS (sickle-hemoglobin C disease). The Thalassemias arise because of a mutation that prevents the expression of either the β-globin gene (β-thalassemia) or the alpha-globin genes (α-thalassemia). As a consequence unusual hetero- and homo-tetrameric Hb pairings arises.

In the β-Thalassemias there is reduced synthesis of β globin ($\beta^+$-thalassemia) or the absence of synthesis of β globin ($\beta^0$-thalassaemia). Clinically mild forms of β-thalassaemia are called thalassemia intermedia. There is also a δβ-thalassaemia which arises from gene fusion and the production of both β and δ chains is diminished). The imbalance in globin chain synthesis with more α-globin than beta-chains leads to precipitation of α-globin in the red cell, which leads to premature destruction of the cell in the bone marrow or the peripheral blood. Excessive α-globin are very damaging to the cell; generating reactive oxygen species (ROS) that destroy cellular proteins, lipids and nucleic acids in the red cell precursors. In addition, tetrameric-α hemoglobin is structurally unstable, with a tendency to denature upon oxidation, filling the cytoplasm and cell membrane with precipitated α-globin chains, free heme, porphyrins and iron, which further propagate ROS production. Erythroid cells have proteolytic pathways to degrade excess free α-globin, but these pathways can be overwhelmed.

In the α-thalassemia's there is the loss of expression of a globin genes; but since humans have four gene copies (two on each parental chromosome see FIG. 1) there is a greater capacity for tolerance. However this also means an equally greater capacity for carriers and as consequence when this has arisen a higher incidence of α-thalassemia within defined populations. Thus, this condition occurs very frequently in Asia; from India to China, including Southeast Asia, and also occurs in the Middle East and Africa.

3 alpha genes functional—patients are silent carriers with no symptoms or signs (α-thalassemia minima α–/α α).

Only 2 alpha genes functional—patients are silent carriers, α-thalassemia minor or α-thalassemia trait but often have microcytosis. The two genes can either occur on the same chromosome (cis-type) or on each of the pair (trans-type). αα/-- ($α^0$ thalassemia) or α-/α- ($α^+$ thalassemia). Cis-type $α^0$ thalassemia trait tends to be found in individuals of Asian descent, while trans-type $α^+$ thalassemia tends to run in individuals of African descent. If a mother is a carrier of $α^0$ thalassemia, her pregnancy is at risk for Bart's hydrops foetalis syndrome, while the worst possible outcome of a pregnancy of a mother with $α^+$ thalassemia is a much milder condition, Hb-H disease.

Only 1 alpha gene functional (α-/--). Gives rise to an excess of β-globin, the excess β globin form tetramers and are deposited as β4 (HbH). HbH is not stable and thermally labile, patients are anaemic and there is splenomegaly.

No alpha genes functional causes early fetal death: The excess of γ-globin chains leads to the depositing of tetramers composed of four gamma chains: $γ_4$ (Hb Bart's). Without the α-globin chains, there can be no HbF or adult hemoglobin (HbA, HbA2) and Hydrops foetalis with stillbirth is the result. There is an increased risk of toxaemia of pregnancy and of post-partum haemorrhage in the carrier $α^0$ thalassemia mother.

Hemoglobin Constant Spring mutation. An unusual case of the silent carrier state is the individual who carries the Hemoglobin Constant Spring mutation. This is an abnormal elongated α-globin due to a termination codon mutation. Individuals who have this mutation have normal red blood cell indices, but can have children who have HbH-Constant Spring disease if the other parent has α-thalassemia trait.

Thus, the physicochemical characteristics and molecular genetic of specific globin proteins/genes is the bases of the molecular testing for the hemoglobinopathies.

The molecular masses of α globin is 15,128 and β globin 15,868; a difference of some 740 da. Thus homo tetrameric complexes of Hb and their hemes (60,000 to 68,000 Da) and derivative trimers (approx. 47,500 Da) and dimers (30,000 to 35,000 Da), of α or β globin will vary in mass by 2960, 2220 and 1480 Da respectively. Theses mass resolutions are within the scope of MALDI-ToF mass spectrometry. Usually the process of MALDI-Tof mass spectrometry dissociates such hemoglobin complexes into the free monomers. Formalin treatment usually "fixes" a protein by forming internal crosslinks via lysine residue side chains forming a methyl bridge with a free hydrogen of an adjacent amide bond. However, formalin will only crosslink between proteins if they are naturally in very close proximity to each other and the correct amino acid side groups align in close proximity. This is the case for the tetrameric complex of Hemoglobin. Thus pre-treatment of whole blood with a formalin solution, such as citrate buffered formal saline will "fix" the Hb complex such that it no longer dissociated and is resolved by MALDI-ToF MS as characteristic m/z of the tetra, tri and dimeric complexes. Thus, the mass pattern characteristic of any particular thalassemia can then be mapped and used as a diagnostic/screening tool for Thalassaemias as described here.

The present application provides a method of detecting a hemoglobinopathy comprising subjecting a blood sample obtained from a subject to direct mass spectral analysis.

"Direct mass spectral analysis" means that the data generated from the mass spectral analysis is used in the method, and not the inferred mass of the components present in the sample. Hemoglobinopathy as used herein refers to any condition caused by a genetic mutation which results in the abnormal expression or structure of one of the globin molecules in the hemoglobin molecule. Examples of hemoglobinopathies include, but are not limited to Sickle cell anaemia, α-thalassemia, β-thalassemia, HbAG, HbA/Enfield, HbH, HbAF, HbS, HbC, HbE, HbD-Punjab, HbO-Arab, HbG-Philadelphia, Hb Constant Spring, Hb Hasharon, Hb Korle-Bu, Hb Lepore, HbM, and Hb Kansas. Preferred hemoglobinopathies are sickle cell anaemia, α-thalassemia, β-thalassemia, HbC, HbE, HbAG, HbA/Enfield, HbH, and HbAF.

The blood sample can be a whole blood sample collected using conventional phlebotomy methods. For example, the sample can be obtained through venipuncture or as a pin prick sample, such as a finger stick or heel prick. The blood sample may be a dried blood spot captured on filter paper or other suitable blood spot capture material.

The blood sample can be an untreated sample. Alternatively, the blood sample may be diluted or processed (concentrated, filtered, etc.).

The blood sample is preferably mixed with either a lysing agent to lyse the red blood cells or initially a crosslinking agent such as citrated formalin for up to 24 hours prior to lysis. Other suitable lysing agents are known to the person skilled in the art. The lysing agent can be mixed with the sample at a suitable concentration such as 1/1 (i.e. 1 part blood to 1 part lysing agent), 1/5, 1/10 or 1/20 or greater. If the blood sample is a dried blood spot, the blood spot capture material on which the sample is dried can be placed in either a lysing agent or citrated formalin to reconstitute the sample. Alternatively the blood spot can be reconstituted in a suitable buffer prior to formalin fixation followed by lysis or direct lysis. Suitable buffers and other protein crosslinking agents are known to the skilled person. A preferred lysing agent is deionised distilled water. Alternatively the sample can be frozen in order to lyse the cells.

The preferred crosslinking agent is citrate buffered formal saline. The sample is preferably mixed with the formalin containing agent at a concentration of 1/5 (i.e. 1 part blood to 5 part citrated formal saline). The sample is allowed to react for a suitable period to allow the red blood cells' globin molecules to become fixed. For example the mixture can be left for 4, 5, 6, 7, 8, 10, 12, 16, 20, 24 hours or more. The sample is preferably left for a minimum of 6 hours Preferably the blood sample is diluted, preferably after lysis. The dilution step effectively purifies the Hb from other components of blood for mass spectral analysis as Hb is the most abundant protein. The blood sample may be diluted 1/10 (i.e. one part sample in 10 parts diluent), 1/166, 1/333, 1/500, 1/1000, 1/2000, 1/2500, 1/8000 or more. Most preferably the sample is diluted 1/2000 i.e. one part blood sample in 2000 parts diluent. Preferably the diluent is 0.1% trifluoroacetic acid in distilled deionised water, or distilled deionized water.

Preferably the blood sample is not processed between fixation, lysis and dilution. In other words the blood sample is only lysed and diluted; or fixed, lysed and diluted. Such processing includes concentrating the proteins of interest e.g. Hb; isolating Hb for example by HPLC or treatment with a chemical agent to disrupt or break intramolecular bonds. In particular, the sample is preferably not treated with a reducing agent. More preferably the sample is not treated with dithiothrietol (DTT).

Preferably the method may comprise comparing the spectra patterns resulting from said direct mass spectral analysis of a sample to mass spectral patterns obtained from direct mass spectral analysis of a blood sample from a normal healthy control to determine whether said patterns from said sample are indicative of a hemoglobinopathy. As used herein a "normal healthy control" is a subject who does not have a hemoglobinopathy.

Preferably, the differences in the patterns of mass spectra are determined by an automated quantitative method that can distinguish between a mass spectrum of a blood sample from a normal healthy control and the mass spectral pattern of a blood sample from a subject with a hemoglobinopathy.

As used herein an "automated quantitative method" refers to the processing of the direct output data from a mass spectrometer to which the sample was subjected by a computer software program.

Methods of generating mass spectra, such as MALDI-Tof MS, are commonly not quantitative techniques. For example the Y axis in these spectra is an indicator of "relative strength" of mass peak within the spectra, but not between mass peaks in one sample versus another sample. In order to overcome this, normalisation needs to render Y axis value comparable between sample spectra. Thus the spectra obtained from the direct mass spectral analysis is preferably normalised. The spectra is subjected to data processing which results in a normalised statistically determined index of relative proportion of mass spectra. This converts the qualitative mass spectra into a quantitative value. Normalization is the process of producing a data structure to reduce repetition and inconsistencies of data. Several normalisation techniques are possible. Typical normalisation methods include percentage of total area at a given point, Square difference and ratio of differences. The percentage difference is calculated as Percentage difference=($Y1-Yref/Yref \times 100\%$)

Wherein Y ref is the minimum Y value of the spectra, and Y1 is Y value for each point.

The square difference is calculated as

Square Difference=$(Y1-Yref)^2$

The ratio difference is calculated as

Ratio Difference=(Ratio 1-Ratio 2).

Thus the data from the mass spectra is manipulated in order to provide a quantitative measure of the qualitative change shown on the spectra.

Preferably, the spectral model is created by a method of data processing which results in a normalised statistically determined index of relative proportion of mass spectra within a set range. This renders all spectra comparable such that the median and centile variability at any given mass value can be modelled. Preferably the range is between about 6,000-700,000 m/z.

For the monovalent forms of the globins the range examined is 6,000-17000 m/z, more preferably 7,500-16,200 m/z. The single charged and/or double charged molecules of red cell globins can be measured. For the singly charged ions, the spectra at the mass/charge range of 15000 m/z to 16200 m/z is examined. For the doubly charged ions, the spectra at the mass/charge range of 5000-8200 m/z, preferably 6000 to 8100 m/z, more preferably 7550 to 8200 m/z or 7550 to 8100 m/z is examined. The table below sets out the position of peaks corresponding to the various globins corresponding to the doubly charged ions.

| Globin chain | M/Z of $[M = 2H]^{2+}$ Based on published sequences and known post translational cleavage |
|---|---|
| A | 7564 m/z |
| µ | 7743 m/z |
| ζ | 7753 m/z |
| θ | 7754 m/z |
| B | 7934 m/z |
| Δ | 7963 m/z |
| $^G\gamma$ | 7999 m/z |
| $^A\gamma$ | 8005 m/z |
| ε | 8102 m/z |

For the multivalent forms of the globins the range examined is 30,000-700,000 m/z, A normalised statistically determined index of relative proportion of mass spectra within a given range can be calculated from using the total area under the curve of mass spectra. This can then be used to calculate the relative intensity.

The area under the curve of mass spectra is calculated by dividing the mass spectra into a plurality of bins of a given number of m/z. As used herein "Bin" has its usual statistical meaning, for example, of being one of a series of ranges of numerical value into which data are sorted in statistical analysis. For example the bins can be 100 m/z, 50 m/z, 25 m/z, 10 m/z or 5 m/z in size. The smaller the size of the bin used, the more refined the method.

The relative intensity (Y Axis value) can be calculated by the "square of difference" method and therefore a comparable Y value given for every bin. In this method, the minimum Y value of the spectra (Y ref) was subtracted from the Y value at every bin and the difference was squared. The formula used to calculate square of difference=$(\gamma 1-\gamma ref)^2$ and the calculated square of difference was then named as "relative intensity".

The relative intensity at each mass bin in a sample can be captured using commercially available statistical tests such as MATLAB®, Stats Direct™ and Origin 8™.

Once the spectra has undergone a method of data processing which results in a normalised statistically determined index of relative proportion of mass spectra, the levels of the globins present can be determined by measuring the relative height of the peaks corresponding to the various globins. Preferably the range is between about 6,000-700,000 m/z. For the monovalent forms of the globins the range examined is 5,000-8,200 m/z, preferably 6,000-17000 m/z, more preferably 7,500-16,200 m/z. For the doubly charged ions, the spectra at the mass/charge range of 5,000-8,200 m/z or 6000 to 8100 m/z, more preferably 7550 to 8100 m/z or 7,550 to 8,200 m/z is examined.

Preferably, the spectra obtained from the direct mass spectral analysis of the sample is compared to a reference spectral model of expected mass between about 6,000-700, 000 m/z or 6,000-100,000 m/z determined from the statistical analysis of a collection of blood samples from normal healthy controls. The "reference spectral model" is the expected mass within a set range, determined from statistical analysis of a collection of blood samples from normal healthy controls. Preferably the range is between about 6,000-700,000 m/z. For the monovalent forms of the globins the range examined is 6,000-17000 m/z, preferably 7,500-16,200 m/z, more preferably 5,000-8,200 m/z. For the doubly charged ions, the spectra at the mass/charge range of 5,000-8,200 m/z or 6000 to 8100 m/z, more preferably 7550 to 8100 m/z or 7,550 to 8,200 m/z is examined. Preferably the spectral model of expected mass between about 5,000-

8,200 m/z or 6,000-8,100 m/z is determined from statistical analysis of a collection of blood samples from normal healthy controls.

Preferably, the spectral model is created by a method of data processing which results in a normalised statistically determined index of relative proportion of mass spectra within a set range. This renders all spectra comparable such that the median and centile variability at any given mass value can be modelled. Preferably the range is between about 6,000-700,000 m/z. More preferably the range is 5,000-8,200 m/z or 6000 to 8100 m/z, most preferably 7550 to 8100 m/z or 7,550 to 8,200 m/z.

Preferably, the spectra obtained from the direct mass spectral analysis of the sample is compared to a disease model, of expected mass between about 6,000-300,000 m/z determined from statistical analysis of a collection blood samples from subjects with a hemoglobinopathy. A parallel "disease" model, is generated from normalised statistically determined index of relative proportion of mass spectra within a set range is created from blood samples obtained from a subject known to have a hemoglobinopathy. Preferably the range is between about 6,000-700,000 m/z. More preferably the range is 5,000-8,200 m/z or 6000 to 8100 m/z, most preferably 7550 to 8100 m/z or 7,550 to 8,200 m/z.

After applying the normalization techniques the spectral value of samples obtained from normal healthy controls and those from subjects suffering from a hemoglobinopathy are compared. The presence of a hemoglobinopathy causes a change in the pattern of the peaks in the normalised spectra, due to a shift in mass caused by the mutation within the globin proteins.

Subjects with sickle cell anaemia have a peak for Sβ at 7920 m/z clearly resolved from β-globin at 7934 m/z and Cβ approx. 7933 m/z. Thus the presence of a peak for Sβ at 7920 m/z is indicative of sickle cell anaemia.

In a subject with Heriditary Persistent fetal hemoglobin blood sample, HbAF, the intensity of β-globin at 7934 m/z is markedly reduced and peak corresponding to Aγ at 8005 m/z is markedly elevated. Baseline elevation of δ and Gγ globins at 7965 and 7996 m/z may also be seen. Thus the presence of a peak corresponding to Aγ at 8005 m/z is indicative of HbAF.

In HbAG there is a mutation at α68Asn-Lys. This causes additional peaks at 7612 and 7645 m/z that may represent fetal alpha-globins ξ and the newly discovered μ. There may also be an elevation of Gγ at 7993 m/z. Thus the presence of peaks at 7612 and 7645 m/z, optionally together with an elevation of Gγ at 7993 m/z can be indicative of HbAG.

HbA/Enfield is a mutation of α89His-Glu. Subjects with this condition have additional peaks at 7612 and 7645 m/z that may represent fetal alpha-globins ξ and the newly discovered μ-globin. There may also be an elevation of δ at 7963 and Gγ at 7993 m/z. Thus the presence of peaks at 7612 and 7645 m/z, optionally together with an elevation of δ at 7963 and Gγ at 7993 m/z can be indicative of HbA/Enfield.

In particular, the ratio of normalized spectral value of samples obtained from normal healthy controls and those from subjects suffering from a hemoglobinopathy can be compared and statistical analysis carried out so that various measures e.g. mean, standard deviation, skewness, upper and lower quartile, median, kurtosis as well as 95th and 5th centile can be calculated.

The difference in relative intensity at each mass bin between samples obtained from normal healthy controls and those from subjects suffering from a hemoglobinopathy can be captured using commercially available statistical tests such as MATLAB®, Stats Direct™ and Origin 8™.

The reference spectral model and the disease model, are then compared by plotting in order to identify 'hot spots' i.e. points of difference between the two models. This may be a decrease or increase in the size of a peak, or the appearance of a peak. The points of difference can then be used to determine the presence of a hemoglobinopathy. Preferably this is done by using a suitable algorithm.

The analysis of the mass spectra can be easily calculated using a suitable computer software program. A computer can also be programmed with the suitable algorithm in order to provide an indication of the presence of a hemoglobinopathy.

Preferably, the mass spectral analysis carried out is matrix-assisted laser desorption/ionization time-of-flight mass spectrometry (MALDI-ToF MS).

When a crosslinking agent is used, the relative percentage abundance of the tetramers, pentamers and trimer present compared to the dimers can be utilised to diagnose the presence of a hemoglobinopathy. There are two forms of tetramer present—the S-tetramer which contain only the globin proteins and the L-tetramer which contains the heme as well as the globins. A mean relative abundance of the fixed S-tetramer compared to the fixed dimer ≥10, preferably ≥15 and/or a mean relative abundance of the fixed L-tetramer compared to the fixed dimer ≥6, preferably ≥10 is indicative of the presence of a hemoglobinopathy. Once this result is achieved the patient can undergo further investigation to identify the specific hemoglobinpathy present.

Also described is a method of detecting a hemoglobinopathy comprising:
  a) obtaining a blood sample from a subject
  b) Dilution and Lysis; or fixation, dilution and lysis of said sample
  c) Subjecting the sample to direct mass spectral analysis
  d) Examining the patterns resulting from said analysis to determine whether said patterns from said sample from a subject are indicative of a hemoglobinopathy.

Preferably the spectra patterns resulting from the analysis are compared to mass spectral patterns obtained from a blood sample from a normal healthy control.

In this specification, the verb "comprise" has its normal dictionary meaning, to denote non-exclusive inclusion. That is, use of the word "comprise" (or any of its derivatives) to include one feature or more, does not exclude the possibility of also including further features. The word "preferable" (or any of its derivates) indicates one feature or more that is preferred but not essential.

All or any of the features disclosed in this specification (including any accompanying claims, abstract and drawings), and/or all or any of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The application will now be described in the following examples which refer to the following figures.

EXAMPLE 1

Method

Sample Processing

The optimal dilution for whole blood is between 1/1000 and 1/2000 in either ddH$_2$O or 0.1% TFA in ddH2O after an initial lysis of sample with ddH$_2$O (1:1 v/v). This dilutional step effectively purifies the Hb from other components of blood for mass spectral analysis as Hb is the most abundant protein. In addition the dilution in ddH2O (or 0.1% TFA/ddH2O) dissociates the constituent globin proteins for resolved analysis by MALDI-ToF Mass spectrometry. Dilutions higher than 1/8000 results in progressively weaker mass spectral signal.

MALDI ToF Mass Spectral Analysis

The optimal matrices are sinnapinic acid (SA), ferulic acid (FA) and alpha 4-cyano hydroxycinnamic acid (CHCA). Sinapinic acid, being the preferred matrix, is mixed or used as pre-coating layer to a mixed drop of 1/1000 to 1/8000 diluted sample (optimal 1/2000). Steel MALDI plates (384 wells) were prepared by pipetting 0.5 µl of matrix solution (sinapinic acid ~20 mg/ml dissolved in 50/50v/v acetonitrile (ACN)/ddH$_2$O and 0.1% trifluoacetic acid (TFA)) and allowed to dry. 0.5 µl of sample, was mixed with SA and spotted on the dry matrix. This was allowed to dry at room temperature for 1 hour before MALDI TOF MS analysis.

The mass spectrometric analysis was carried out using a Shimadzu Axima plus MALDI mass spectrometer: the pulse nitrogen laser ($\lambda_{max}$=337 nm), was fired at 75 to 80% arbitrary units of power. The ions were accelerated by a 20 kV electrical field down a 1.2 m linear tube and detected by a micro-channel plate detector at a sampling rate of 500 MHz. Spectra were generated by summing 20-30 laser shots. A positive linear mode with delayed extraction was used in order to acquire the spectra.

The instrument was internally calibrated whereby a 1/1000 diluted sample of blood was spiked with 10 pmoles/ul Cytochrome C (1:2, v/v) The two points calibration generated was at [M+H]+=12 361 m/z and [M+2H]2+=6181 m/z.

A mass spectral region of between 6,000 and 17,000 m/z was collected and analysed and in particular the range of 6000 to 8100 m/z or 6000 to 8200 m/z examined for doubly charged globin proteins.

These are characterised both in respect to centroid mass assignment and relative peak intensity either as comparative normalised peak height or normalised peak area in the spectral range examined.

Results

Identification of Globins

The best resolution was achieved in the m/z range 6000 to 8200 corresponding to $[M=2H]^{2+}$ ions.

| Peak assignment to Globin chains | M/Z of $[M = 2H]^{2+}$ |
| --- | --- |
| A | 7564 m/z, ± 5 m/z |
| Acetyl and Carbonyl adducts of α-globin | 7594 m/z, ± 5 m/z |
| Glycated α | 7645 m/z, ± 5 m/z |
| Matrix (SA) adduct of α-globin | 7671 m/z, ± 5 m/z |
| $^s$β | 7921 m/z |
| B | 7936 m/z, ± 5 m/z |
| Δ | 7965 m/z, ± 5 m/z |
| Gγ | 7996 m/z, ± 5 m/z |
| Aγ | 8005 m/z, ± 5 m/z |
| Glycated β | 8017 m/z, ± 5 m/z |
| Matrix (SA) adduct of β-globin | 8039 m/z ± 5 m/z |
| Marker 8088 m/z possibly ε-globin | 8088 m/z ± 5 m/z |

Pathological Sample Spectral Patterns

As a general finding in all samples in which a hemoglobinopathy was present peaks corresponding to either mutated or fetal globin genes where seen. This was not the case for a non-affected blood samples.

Figure 2:
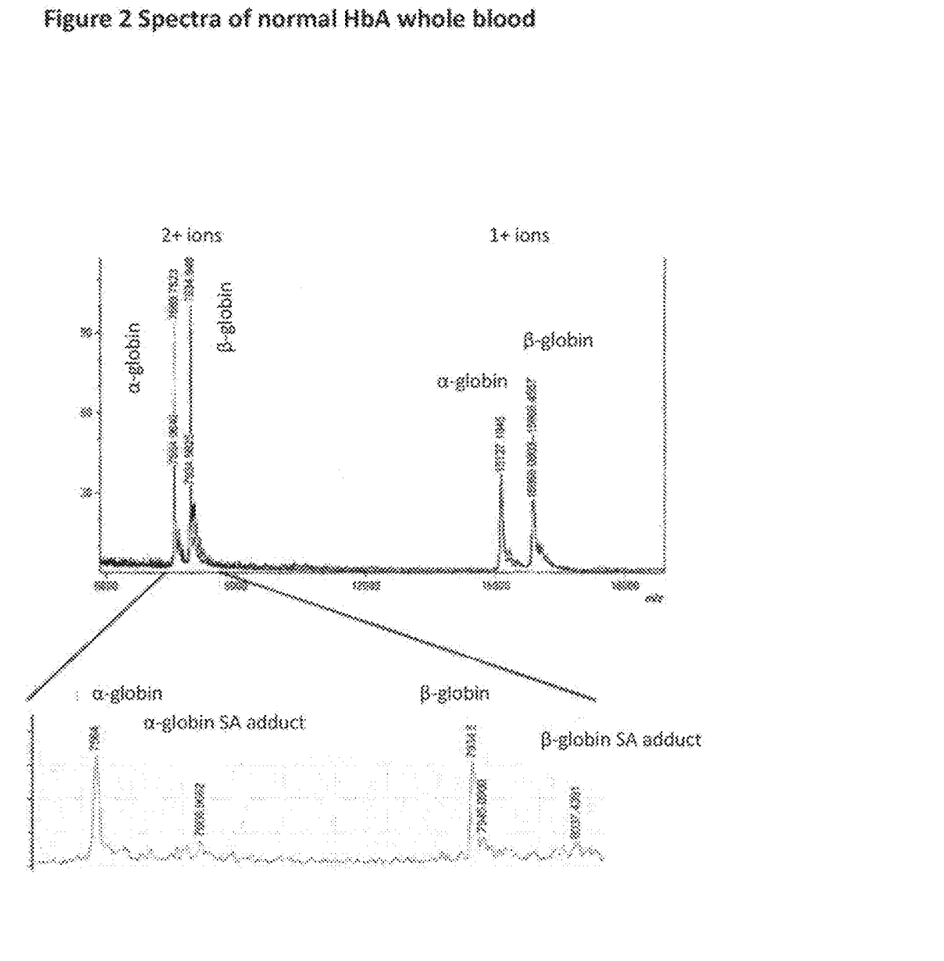
FIG. 2 shows a spectra of HbA whole blood

A normal adult Hb sample reveals peaks for α-globin and β-globin with other globins found in HbA2 and HbF (δ, Gγ and Aγ) barely detected. (FIG. 2).

Figure 3:
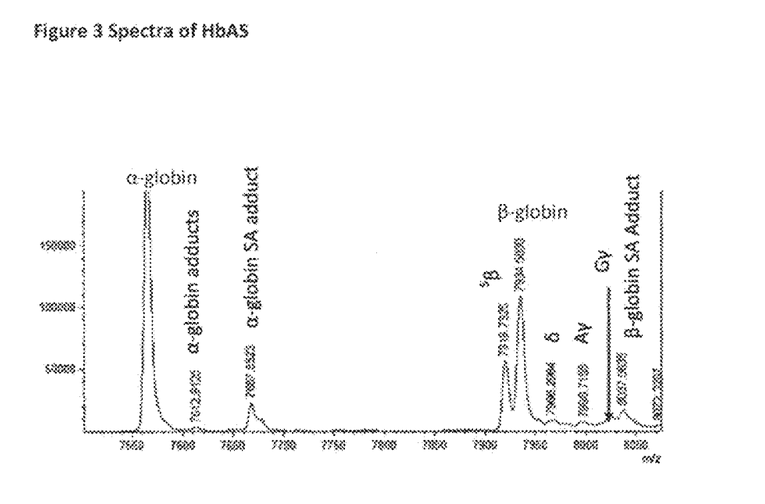
FIG. 3 shows a spectra of HbAS
Figure 4:
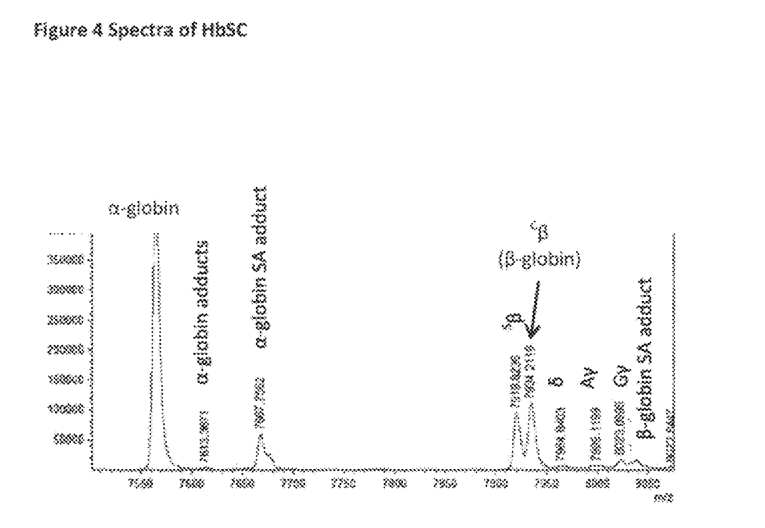
FIG. 4 shows a spectra of HbAC

Hb S—Sickle cell diseases (FIGS. 3 & 4)

Blood sample from a patient with sickle cell trait (HbAS) revealed normal and SA adducted α-globin peaks and a peak for Sβ at 7920 m/z clearly resolved from β-globin at 7934 m/z and Cβ approx. 7933 m/z. Baseline elevation of δ and Gγ globins at 7965 and 7996 m/z was evident as was a new peak at 8023 m/z.

Figure 5:
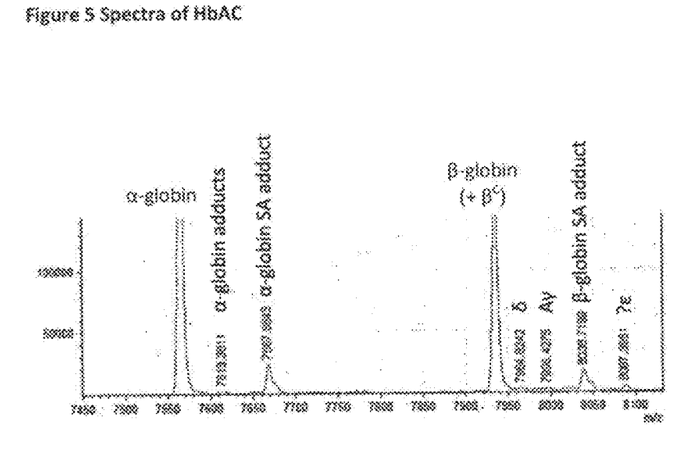
FIG. 5 shows a spectra of HbAC

HbAC (FIG. 5)

Blood sample from a patient carrying HbC trait showed a single normal and SA adducted α-globin peaks. Baseline elevation of δ and Gγ globins at 7965 and 7996 m/z was evident, but β-globin at 7934 m/z was not resolved from Cβ approx. 7933 m/z.

Figure 6:
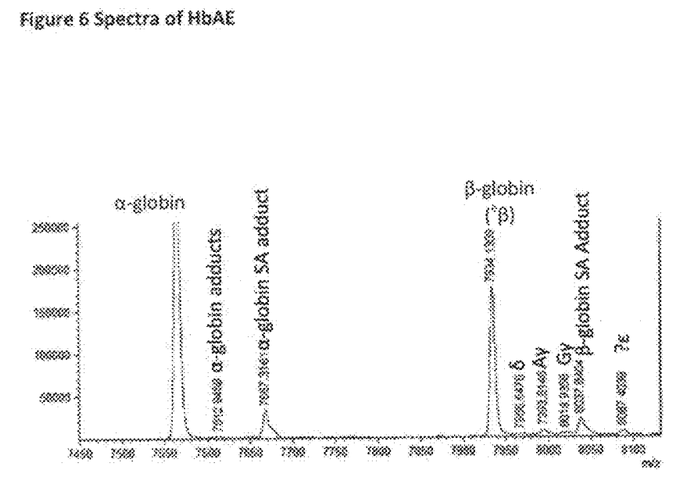
FIG. 6 shows a spectra of HbAE

HbAE (FIG. 6)

Blood samples from a patient carrying HbE trait showed a single normal and SA adducted α-globin peaks. Baseline elevation of δ and Gγ globins at 7965 and 7996 m/z was evident, but β-globin at 7934 m/z was not resolved from $\beta^E$ also approx. 7933 m/z.

Figure 7:
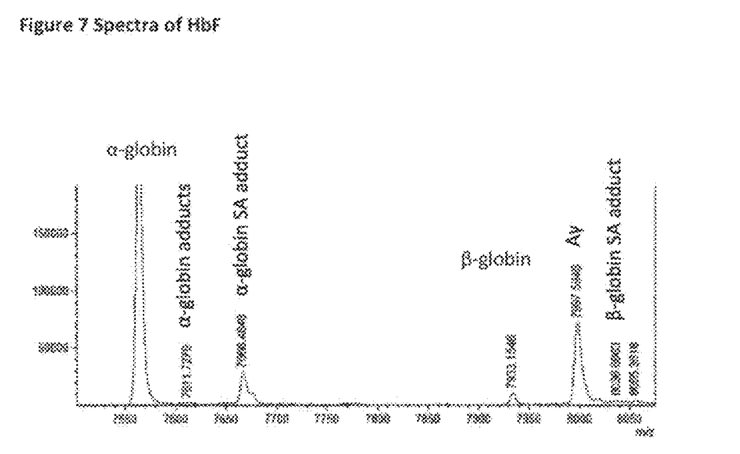
FIG. 7 shows a spectra of HbF

HbAF (FIG. 7)

Figure 8:
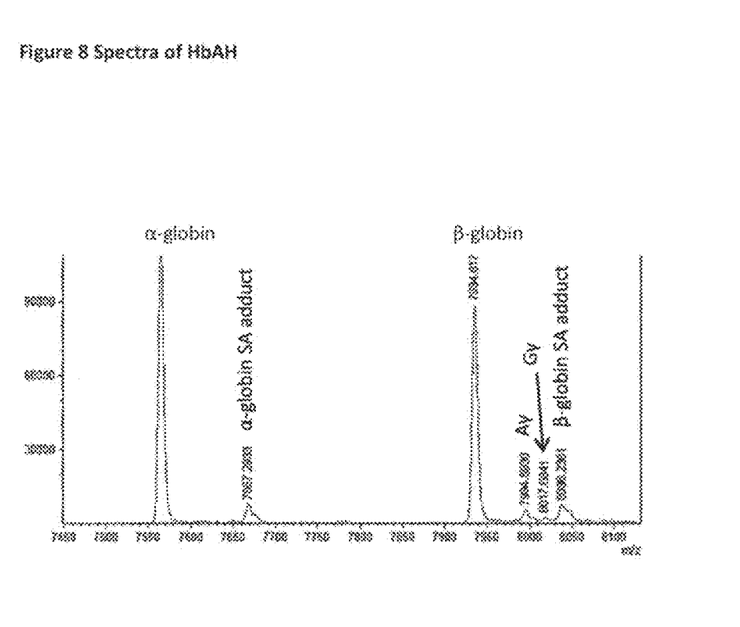
FIG. 8 shows a spectra of HbH

Heriditary Persistant fetal hemoglobin blood sample, HbAF, showed a single normal and SA adducted α-globin peaks. The intensity of β-globin at 7934 m/z was markedly reduced and Aγ at 8005 mz was markedly elevated. Baseline elevation of δ and Gγ globins at 7965 and 7996 m/z was also seen, HbH disease (α-/- -) α-thalassemia (FIG. 8)

Blood sample from HbH revealed a peak showed a single normal and SA adducted α-globin peaks at 7564 and 7667 m/z. β-globin was evident at 7934 m/z and baseline elevation of Gγ and Aγ globins at 7996 & 8017 m/z was evident.

Figure 9:
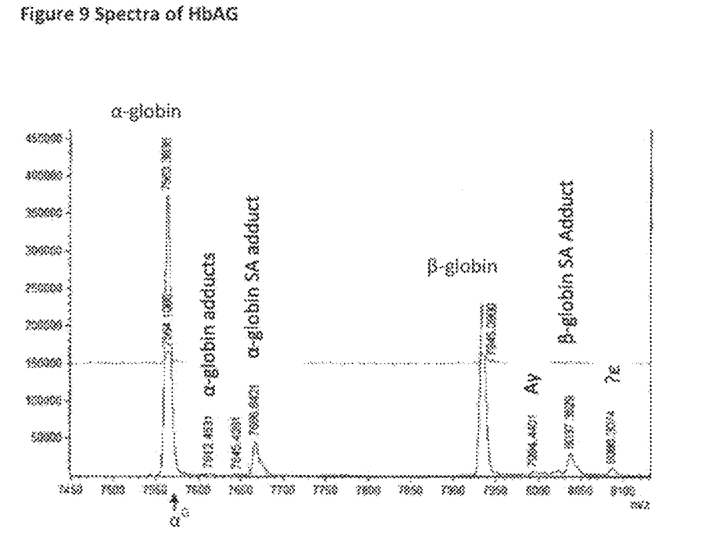
FIG. 9 shows a spectra of HbAG
Figure 10:
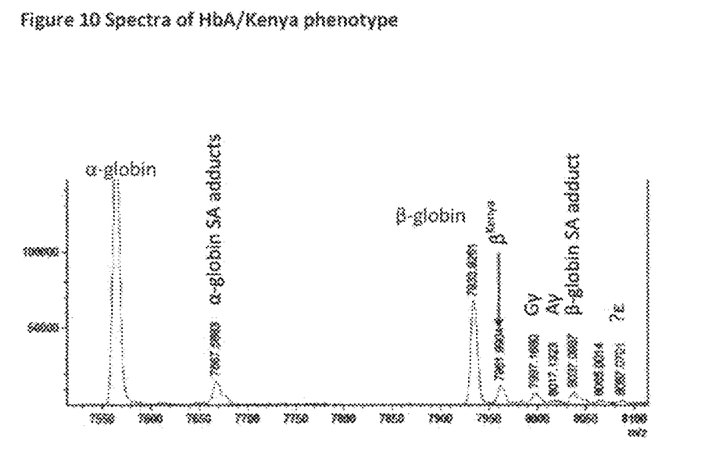
FIG. 10 shows a spectra of HbA/Kenya

Expressed α- and β globin mutations (FIGS. 9 & 10)

HbAG is caused by the mutation in α globin at α68Asn-Lys. An α-globin was seen at 7564 m/z, SA adducted α at 7667 m/z but additional peaks at 7612 (unknown) and 7645 m/z (glycated α-globin) were seen. The β globin at 7933 m/z was accompanied with an elevation of Gγ at 7993 m/z HbA/Kenya phenotype is a a fusion of Gγ and β showed similarly An α-globin was seen at 7564 m/z, SA adducted α at 7667 m/z but additional peaks at 7961 m/z, coinciding with the peak for δ at 7963 m/z, probably represent the fusion β globin. The β globin at 7933 m/z was accompanied with an elevation of Gγ at 7993 m/z.

Figure 11A:
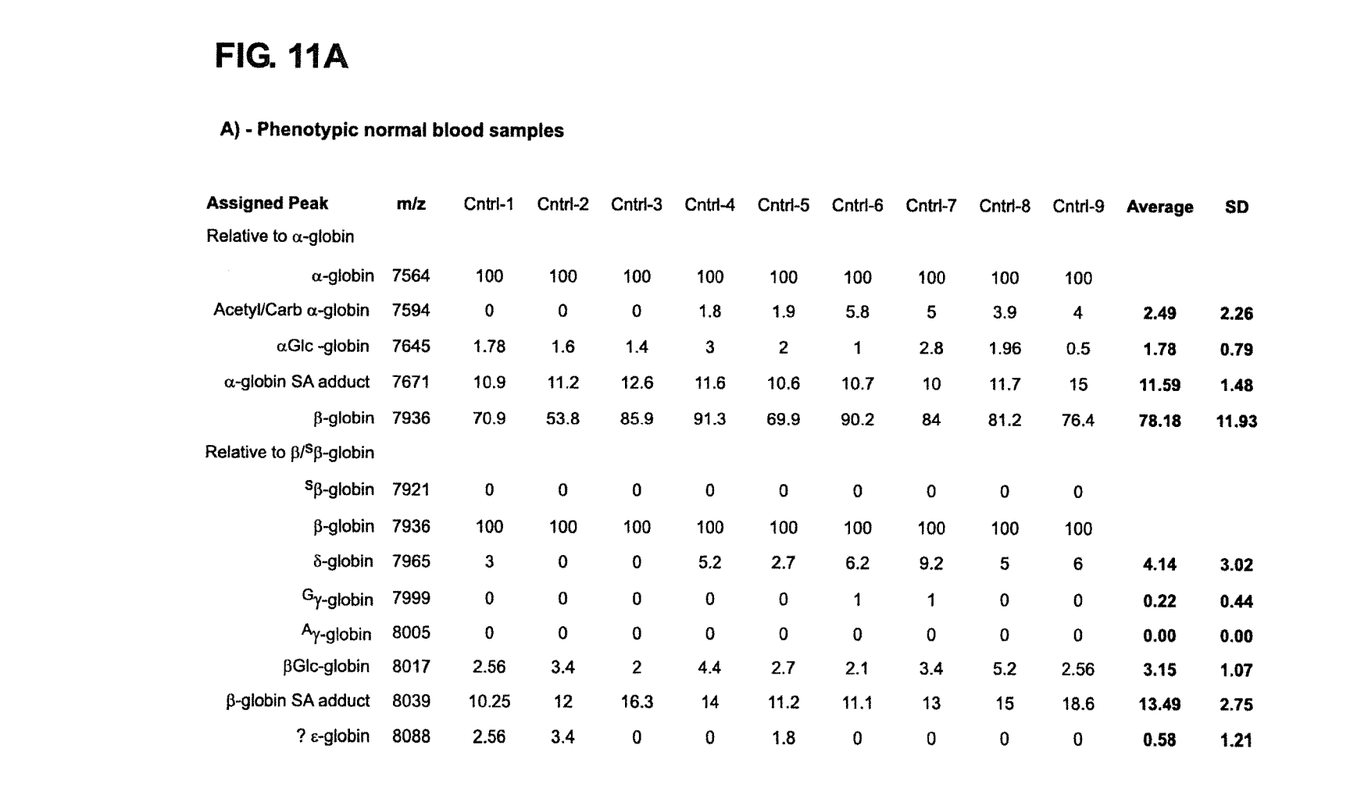
FIGS. 11A and 11B show tabulated Comparison of spectra for phenotypic normal and abnormal samples
Figure 11B:
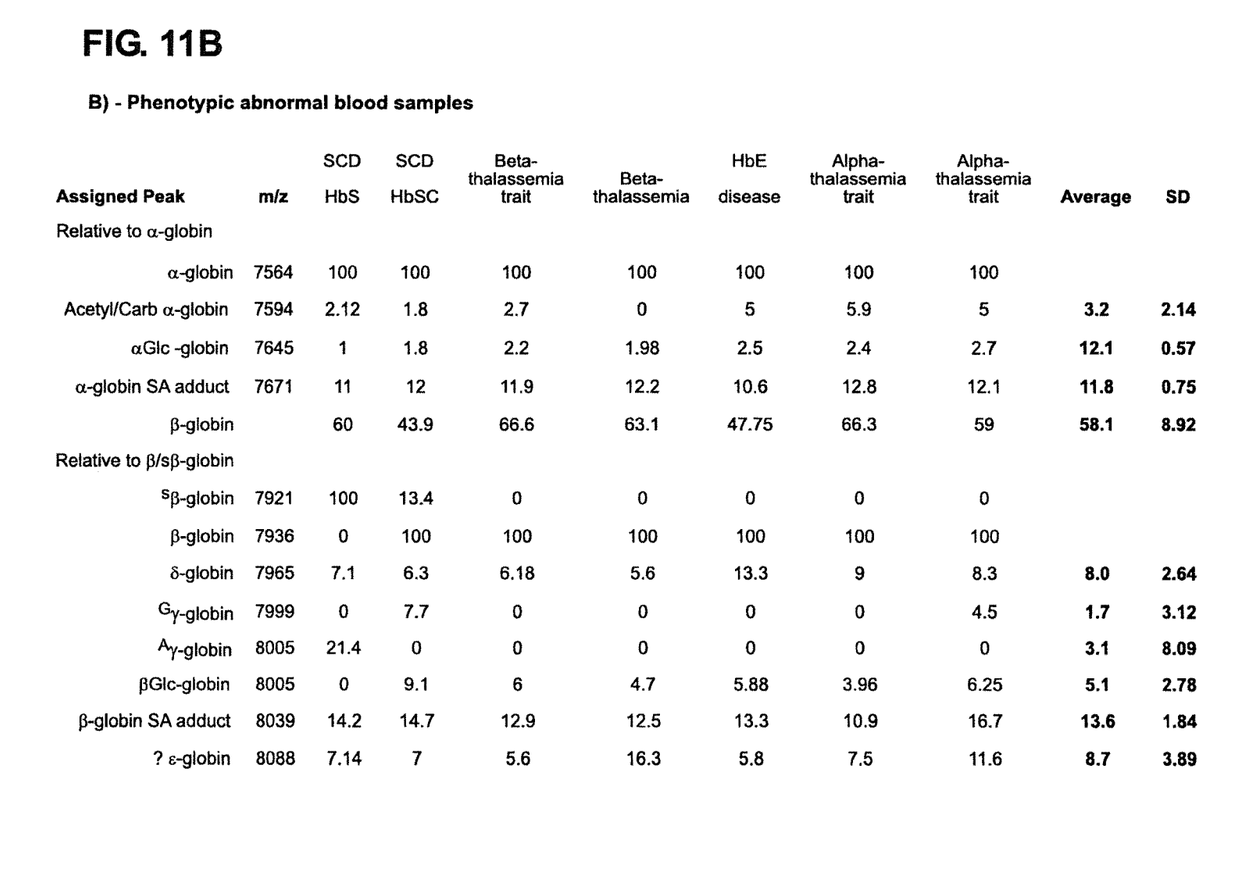

Comparison of Phenotypic Normal and Abnormal Samples (FIGS. 11A, 11B)

A further 9 phenotypically normal blood samples and 9 phenotypically abnormal blood samples (a homozygote HBS sickle cell disease, a heterozygote HBSC Sickle cell disease, 2 phenotypic alpha thalassemia traits, a beta-thalassemia and a beta-thalassemia trait and HbE disease) were examined.

A feature of all hemoglobinopathies and carriers is elevated proportions of δ-globin, γ-(G and A) globins and marker m/z 8088 (possibly ε-globin), compared to non-affected individuals. In addition the ratio of β-globin to α-globin is lower in affected and carriers compared phonotypic normal blood samples (see table 3) mean for unaffected This probably reflects the change in transcriptions arising from the Beta-globin gene cluster to additionally express δ and fetal globins as demonstrated.

Classic $^s\beta^s\beta$ homozygote is detectable by a mass shift in the predominant beta-globin peak to 7921 m/z, whilst $^s\beta^c\beta$ sickle cell disease shows a significant lower 7921 m/z peak but dominant peak at 7936 m/z of β($^c$β) globin similar to a sickle carrier. However $^s\beta^s\beta$ Sickle disease has elevated δ and γ-globins and marker masses (i.e 8088 m/z possibly ε-globin).

Both phenotypic beta-thalassemia and beta-thalassemia trait samples were characterized by elevated aberrant peaks at 8088 m/z (possible ε-globin), moderate elevated δ-globins and reduced β/α globin ratio. This pattern was similar for HbE disease but a more marked elevation of δ-globin was seen.

Both phenotypic samples of alpha thalassemia trait demonstrated elevated aberrant peaks at 8088 m/z (possible ε-globin), elevated δ and γ globins.

EXAMPLE 2

Formalin Fixed Samples

Method
Sample Processing

Whole Blood sample is mixed 1 part to five parts with citrate buffered formal saline for a minimum of six hours. This is then diluted between 1/166 and 1/333 in either ddH2O or 0.1% TFA in ddH2O. This dilutional step effectively purifies the Hb from other components of blood for mass spectral analysis as Hb is the most abundant protein.

Dilutions higher than 1/8000 results in progressively weaker mass spectral signal.

MALDI ToF Mass Spectral Analysis

The optimal matrices are sinnapinic acid (SA), ferulic acid (FA) and alpha 4-cyano hydroxycinnamic acid (CHCA). Sinapinic acid being the preferred matrix is mixed or used as pre-coating layer to a mixed drop of 1/1000 to 1/8000 diluted sample (optimal 1/2000). Steel MALDI plates (384 wells) were prepared by pipetting 0.5 μl of matrix solution (sinapinic acid −20 mg/ml dissolved in 50/50 v/v acetonitrile (ACN)/ddH$_2$O and 0.1% trifluoracetic acid (TFA)) and allowed to dry. 0.5 μl of sample, was mixed with SA and spotted on the dry matrix. This was allowed to dry at room temperature for 1 hour before MALDI TOF MS analysis. The mass spectrometric analysis was carried out using a Shimadzu Axima plus MALDI mass spectrometer: the pulse nitrogen laser ($\lambda_{max}$=337 nm), was fired at 80 to 100% arbitrary units of power. The ions were accelerated by a 20 kV electrical field down a 1.2 m linear tube and detected by a micro-channel plate detector at a sampling rate of 500 MHz. Spectra were generated by summing 20-30 laser shots. A positive linear mode with delayed extraction was used in order to acquire the spectra.

A mass spectral region of between 30,000 and 70,000 m/z was collected and analysed. These are characterised both in respect to centroid mass assignment and relative peak intensity either as comparative normalised peak height or normalised peak area in the spectral range examined.

Sample Spectral Patterns

As a general finding peaks corresponding to separated monomeric globins, dimers, trimers and tetramers and complexes such as pentamers are found. Individual peaks or mass distribution of broad peaks corresponding to compositional dimers, trimers, tetramers and larger complex correspond to the relative mass representations of the various globin pairing. i.e. for dimers, αβ, αα, ββ, αδ, αAγ, αGγ etc. Similarly the large complex mass distribution within the broad peaks represent relative composition of trimeric, tetrameric, pentameric and other complex combinations of the individual globins.

Figure 12:
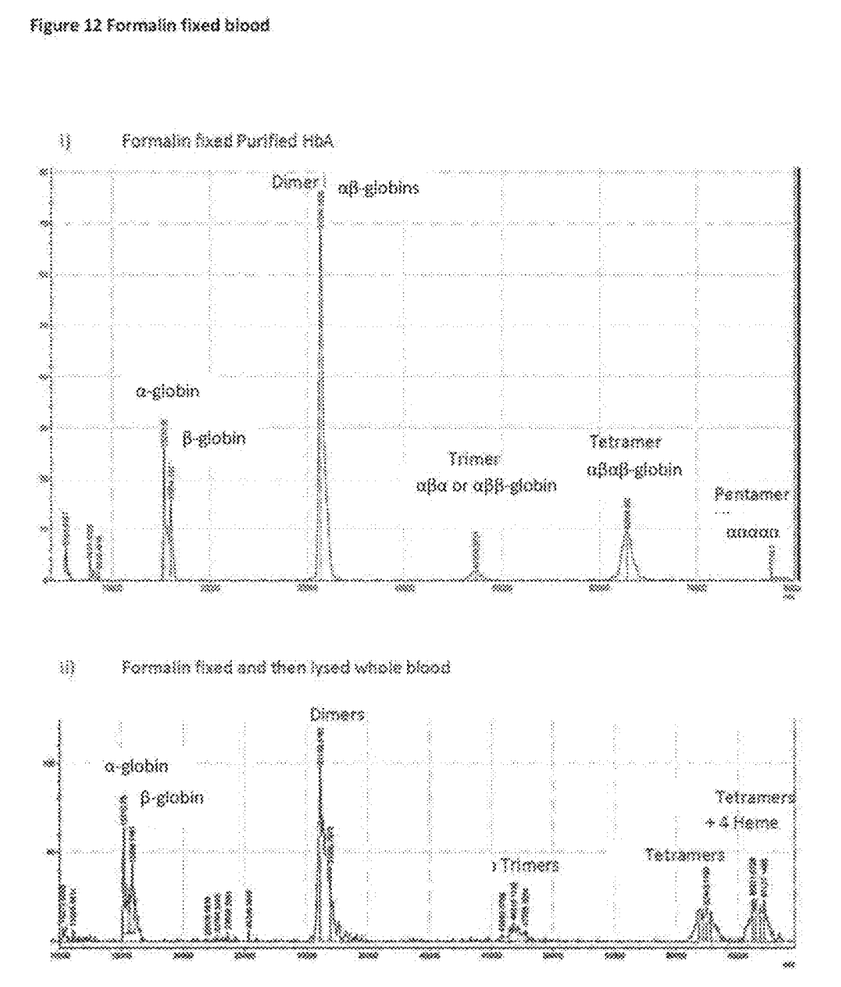
FIG. 12 shows the mass spectral pattern between 30,000 to 70,000 m/z of formalin fixed purified HbA and formalin fixed whole blood HbA

Formalin Fixed HbA and Whole Blood Samples (FIG. 12).

A normal purified adult HbA sample reveals peaks for α-globin and β-globin with other globins found in HbA2 and HbF (δ, Gγ and Aγ) not detected. Specific oligomeric pairing of globins were detected dimers central maxima 31396 m/z corresponding to α-β globin; trimers central maxima of 47308 m/z corresponding to ααβ and αββ; tetramers central maxima 62858 m/z corresponding to and αβββ; and a complex of pentamers including an acentric mass maxima at 77732 m/z corresponding to ααααα.

Whole blood, fixed with formalin and then lysed similarly revealed the monomeric globins (15000 to 17000 m/z), Hb dimers (31000-33000 m/z), Hb trimers (45,000-45800 m/z), Hb tetramers (61000-64000 m/z) and tetramers plus four heme prosthetic units (66,000-68000 m/z).

Figure 13:
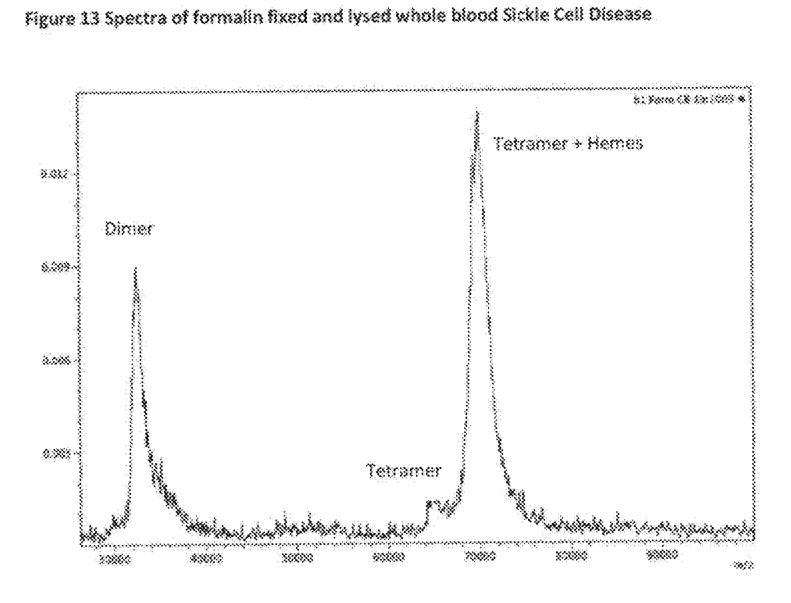
FIG. 13 shows a spectra of formalin fixed Sickle cell disease (SSD) blood sample
Figure 14:
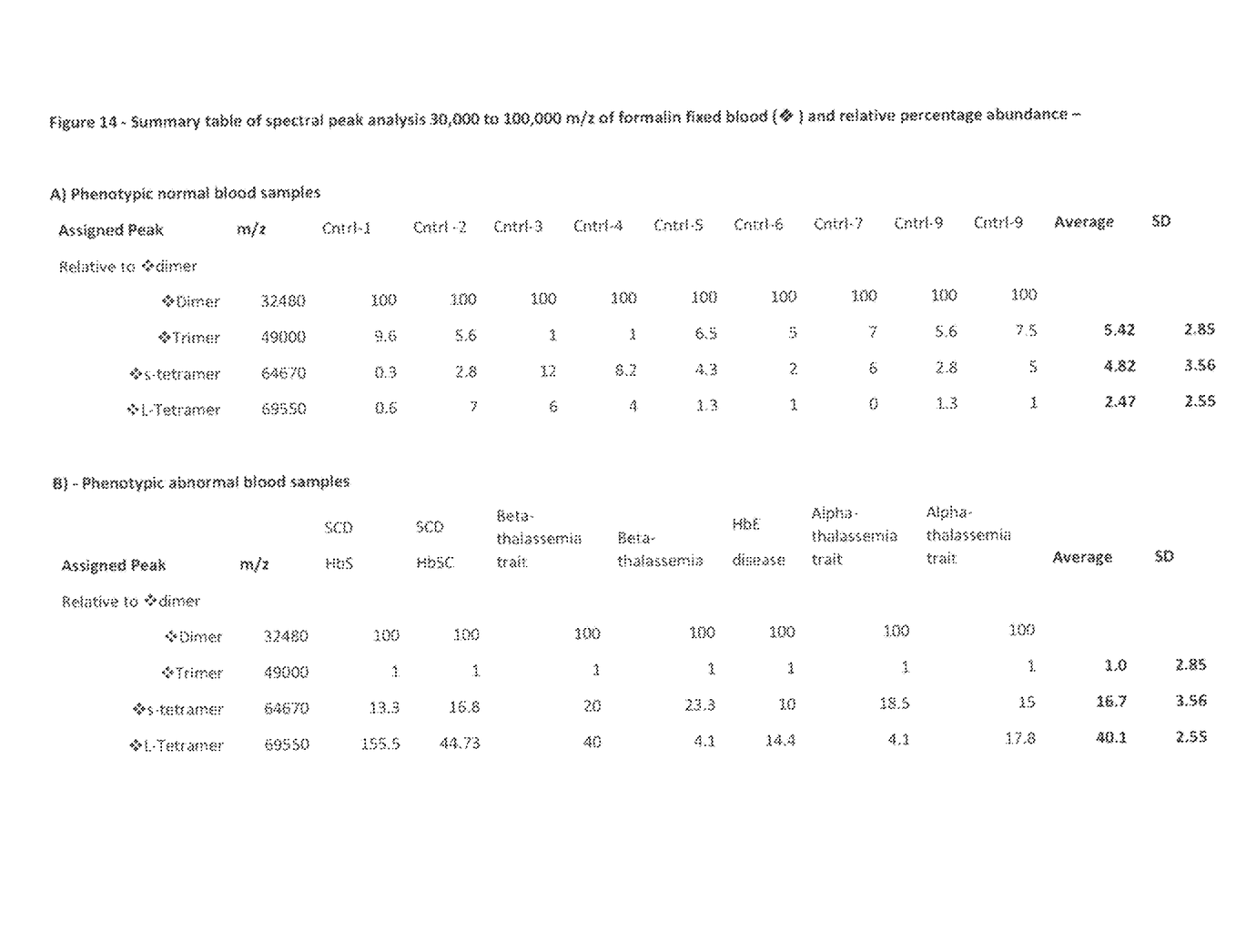
FIG. 14 shows tabulated Comparison of formalin fixed spectra for phenotypic normal and abnormal samples

Comparison of Phenotypic Normal and Abnormal Samples (FIGS. 13 and 14)

A further 9 phenotypically normal blood samples and 9 phenotypically abnormal blood samples (a homozygote HBS sickle cell disease, a heterozygote HBSC Sickle cell disease, 2 phenotypic alpha thalassemia traits, a beta-thalassemia and a beta-thalassemia trait and HbE disease) were examined.

A feature of all the hemoglobinopathies is an altered profile in the relative Intensity ratios of formalin fixed dimeric globins to tetramer/oligomers (FIG. 13). This is most dramatic in sickle cell disease (see FIG. 14) but also seen in beta- and alpha-thallasemia's including trait which have double the ratio of tetramer/oligomers compared to unaffected.

Discussion

The major problem facing clinical laboratories in the identification of hemoglobinopathies is that results are often presumptive rather than definitive so there is a need to either confirm or differentiate positive results from one test with another test. In order to completely screen a population or confirm a specific diagnosis a conglomeration of several methods are used from sickling tests, microscopic examination of blood smears, Hb electrophoresis, capillary electrophoresis and high performance liquid chromatography. This is all very costly in the volume of sample, time taken and resources. There is a need for tests which are quicker and cost effective especially if a national screening policy was to be introduced.

CONCLUSION

Pin prick and blot spots can be rapidly screened for sickle cell and other potential hemoglobinopathies by MALDI-ToF mass spectrometry. Samples are lysed and diluted 1000 fold or more in water. Doubly charged ions of the constituent globins are sufficiently and reproducibly resolved by MALDI-ToF MS to reveal characteristic m/z of Sβ. Furthermore, other hemoglobinothies are characterised by detection of elevated m/z signal from fetal globins. These fetal globins may be expressed, under stressed conditions, in an attempt to compensate for defective α and β globin gene expression and act as a biomarker of hemoglobinopathy. However, if fixed by formalin or other suitable crosslinking agent, and then lysed the constituent tetrameric, dimeric pairing and any other oligomeric grouping of the globins (exampled are trimers and pentamers) are revealed and can indicate excessive and unusual α or β globin oligomeric pairing characteristic of α and β Thalassemias.

The invention claimed is:

1. A method of detecting a hemoglobinopathy comprising subjecting a blood sample obtained from a subject to matrix-assisted laser desorption/ionization spectrometry time-of-flight mass spectrometry (MALDI-ToF MS), wherein the sample subjected to MALDI-ToF MS is not processed other than lysis or dilution, and wherein the spectra is examined for doubly charged ions of globin proteins.

2. The method as claimed in claim 1 wherein the blood sample is mixed with a lysing agent prior to direct mass spectral analysis.

3. The method as claimed in claim 2 wherein the lysing agent comprises formalin.

4. The method as claimed in claim 1 wherein the sample is diluted prior to direct mass spectral analysis.

5. The method as claimed in claim 1 wherein the hemoglobinopathy is selected from Sickle cell anaemia, α-thalassemia, β-thalassemia, HbAG, HbA/Enfield, HbH, HbAF, HbS, HbC, HbE, HbD-Punjab, HbO-Arab, HbG-Philadelphia, Hb Constant Spring, Hb Hasharon, Hb Korle-Bu, Hb Lepore, HbM, and Hb Kansas.

6. The method according to claim 1, wherein the spectra obtained from the direct mass spectral analysis is normalised.

7. The method according to claim 1, wherein the spectra obtained from the direct mass spectral analysis is examined in the range of 5,000-8,200 m/z.

8. The method according to claim 1, further comprising comparing the patterns resulting from said direct mass spectral analysis of said sample to mass spectral patterns obtained from direct mass spectral analysis of a blood sample from a normal healthy control to determine whether said patterns from said sample are indicative of a hemoglobinopathy.

9. The method according to claim 1, wherein the spectra obtained from the direct mass spectral analysis of the sample is compared to a reference spectral model of expected mass between about 5,000-8,200 m/z determined from statistical analysis of a collection blood samples from normal healthy controls.

10. The method according to claim 1, wherein the spectra obtained from the direct mass spectral analysis of the sample is compared to a disease model, of expected mass between about 5,000-8,200 m/z determined from statistical analysis of a collection blood samples from subjects with a hemoglobinopathy.

* * * * *